(12) United States Patent
Chilakala et al.

(10) Patent No.: US 11,278,634 B1
(45) Date of Patent: Mar. 22, 2022

(54) STABLE PARENTERAL COMPOSITION OF LACOSAMIDE

(71) Applicant: EXTROVIS AG, Baar (CH)

(72) Inventors: Krishna Mohan Chilakala, Hyderabad (IN); Hanumantha Rao Kamma, Baar (CH); Janos Vaczi, Kuessnacht am Rigi (CH)

(73) Assignee: EXTROVIS AG, Baar (CH)

( * ) Notice: Subject to any disclaimer, the term of this patent is extended or adjusted under 35 U.S.C. 154(b) by 0 days.

(21) Appl. No.: 17/327,308

(22) Filed: May 21, 2021

(30) Foreign Application Priority Data

Feb. 12, 2021 (IN) .............................. 202121006066

(51) Int. Cl.
*A61L 2/00* (2006.01)
*A61K 31/165* (2006.01)

(52) U.S. Cl.
CPC .......... *A61L 2/0023* (2013.01); *A61K 31/165* (2013.01); *A61L 2202/21* (2013.01)

(58) Field of Classification Search
CPC .................................................. A61K 31/165
See application file for complete search history.

(56) References Cited

U.S. PATENT DOCUMENTS

| | | | | |
|---|---|---|---|---|
| 8,907,132 | B2 * | 12/2014 | Reddy | ..................... C03C 17/22 |
| 2015/0290080 | A1 | 10/2015 | Weikart et al. | |
| 2015/0297800 | A1 | 10/2015 | Weikart et al. | |
| 2021/0114921 | A1 * | 4/2021 | Depoilly | ............... C07C 233/05 |

FOREIGN PATENT DOCUMENTS

| | | |
|---|---|---|
| CN | 104771356 A | 7/2015 |
| WO | 1997/033861 A1 | 9/1997 |
| WO | 2005/120476 A2 | 12/2005 |
| WO | 2006/079547 A3 | 9/2006 |
| WO | 2007/144196 A2 | 12/2007 |
| WO | 2008/000513 A2 | 1/2008 |
| WO | 2009/053070 A1 | 4/2009 |
| WO | 2012/037457 A1 | 3/2012 |
| WO | 2013/007698 A1 | 1/2013 |
| WO | 2013/071138 A1 | 5/2013 |
| WO | 2014/117089 A1 | 7/2014 |
| WO | 2014/164928 A1 | 10/2014 |
| WO | 2019/240697 A2 | 12/2019 |

OTHER PUBLICATIONS

Vimpat Prescribing Information (Vimpat (lacosamide) Tablets and Injection, Approved Labeling Text—NDA 22-253 and 22-254 dated Oct. 28, 2008 (Year: 2008).*
Vimpat Assessment Report, European Medicines Agency, Committee for Medicinal Products for Human Use, Assessment report, Vimpat, publication date: 2011 (Year: 2011).*
Sciencedirect, Heat Sterilisation, Heat Sterilisation—an overview, ScienceDirect Topics (Year: 2020).*
Vimpat, Patient Prescribing Information, Revised Nov. 2020.
UCB Pharma SA, "Assessment Report for Vimpat Procedure No. EMEA/H/C/000863" https://www.ema.europa.eu/en/documents/assessment-report/vimpat-epar-public-assessment-report_en.pdf, pp. 1-52 (2008).

* cited by examiner

*Primary Examiner* — Mark V Stevens
*Assistant Examiner* — Alparslan Asan
(74) *Attorney, Agent, or Firm* — Medler, Ferro, Woodhouse & Mills PLLC

(57) ABSTRACT

In some embodiments, the disclosure provides a method of making a sterile lacosamide composition, the method comprising; (a) obtaining a composition comprising (i) about 5 mg/mL to about 20 mg/mL lacosamide, (ii) about 5 mg/mL to about 12 mg/mL sodium chloride, and (iii) water, (b) placing the composition of (a) into a glass vial, wherein the glass vial has an ammonium sulfate coating, (c) sealing the composition inside the glass vial; and (d) autoclaving the sealed glass vial of (c) at 121° C. at 15 lbs pressure for 15 minutes, wherein the pH of the composition in (d) is substantially the same as the pH of the composition after (a), and wherein the composition of (d) comprises less than about 0.2% (wt/wt) of Impurity A, Impurity B, Impurity C, Impurity D, Impurity E or Impurity F.

10 Claims, No Drawings

STABLE PARENTERAL COMPOSITION OF LACOSAMIDE

In some embodiments, the disclosure provides a method of making a sterile lacosamide composition, the method comprising; (a) obtaining a composition comprising (i) about 5 mg/mL to about 20 mg/mL lacosamide, (ii) about 5 mg/mL to about 12 mg/mL sodium chloride, and (iii) water, (b) placing the composition of (a) into a glass vial, wherein the glass vial has an ammonium sulfate coating, (c) sealing the composition inside the glass vial; and (d) autoclaving the sealed glass vial of (c) at 121° C. at 15 lbs pressure for 15 minutes, wherein the pH of the composition in (d) is substantially the same as the pH of the composition in (a), and wherein the composition of (d) comprises less than 0.2% (wt/wt) of Impurity A, Impurity B, Impurity C, Impurity D, Impurity E or Impurity F.

BACKGROUND

Lacosamide (Formula I) is commercially available as VIMPAT® (Harris FRC Corporation, Smyrna, GA) for the treatment of partial-onset seizures in patients 4 years of age and older, and as adjunctive therapy in the treatment of primary generalized tonic-clonic seizures in patients 4 years of age and older.

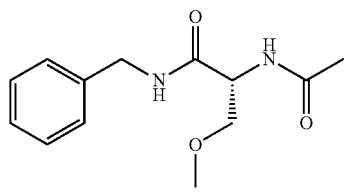

Formula I

Lacosamide therapy can be administered either orally or intravenously. Solution for infusion is an alternative for patients when oral administration is not feasible. Lacosamide injection can be administered intravenously without further dilution or may be mixed with diluents such as Sodium Chloride Injection 0.9% (w/v), Dextrose Injection 5% (w/v) or Lactated Ringer's Injection. It is recommended that the diluted solution not be stored for more than 4 hours at room temperature. The recommended infusion duration is 30 to 60 minutes; however, infusions as rapid as 15 minutes can be administered in adults if required. Infusion durations less than 30 minutes are generally not recommended in pediatric patients. Lacosamide injection is available in a strength of 200 mg/20 mL, as a clear, colorless sterile solution packaged in single-dose vials.

The European Public Assessment Report available online for Vimpat® injection reports that lacosamide solution for infusion 10 mg/mL is manufactured by preparing an aqueous solution of lacosamide, sodium chloride for tonicity adjustment and diluted hydrochloric acid for pH-adjustment to the target pH. Afterwards, this solution is sterile filtered and filled into vials under aseptic conditions. The solution is tested for bioburden before sterilization by filtration. The manufacturing process is validated with emphasis on the compounding, sterile filtration and filling steps. Typically, regulatory agencies prefer parenteral or injectable products that are terminally sterilized over products manufactured by aseptic processes, making an exception only when terminal sterilization can cause product degradation. Terminal sterilization provides lethal treatment of microorganisms, is easily reproducible, is relatively easy to validate, and involves no post sterilization handling as opposed to aseptic processing, wherein extensive handling under controlled environment is essential, which could lead to breach in sterility. Terminal sterilization also avoids the drawbacks associated with aseptic processing, including larger drug recalls for the lack of sterility and control of many variables.

BRIEF SUMMARY OF THE INVENTION

In some embodiments, the disclosure provides a method of making a sterile lacosamide composition, the method comprising; (a) obtaining a composition comprising (i) about 5 mg/mL to about 20 mg/mL lacosamide, (ii) about 5 mg/mL to about 12 mg/mL sodium chloride, and (iii) water, (b) placing the composition of (a) into a glass vial, wherein the glass vial has an ammonium sulfate coating, (c) sealing the composition inside the glass vial; and (d) autoclaving the sealed glass vial of (c) at 121° C. at 15 lbs pressure for 15 minutes, wherein the pH of the composition in (d) is substantially the same as the pH of the composition (a), and wherein the composition of (d) comprises less than 0.2% (wt/wt) of Impurity A, Impurity B, Impurity C, Impurity D, Impurity E or Impurity F.

In some embodiments, the disclosure is directed to a method of making a sterile lacosamide composition, the method comprising; (a) obtaining a composition comprising (i) lacosamide, (ii) sodium chloride, and (iii) water, (b) placing the composition of (a) into a glass vial, wherein the glass vial has an ammonium sulfate coating, (c) sealing the composition inside the glass vial; and (d) sterilizing the sealed glass vial of (c).

In some embodiments, the pH of the composition in (d) is substantially the same as the pH of the composition in (a). In some embodiments, the pH of the composition of (a) and the pH of the composition after (d) have a difference of less than 1.0 unit. In some embodiments, the pH of the composition of (a) and the pH of the composition after (d) have a difference of less than 0.6 units. In some embodiments, the composition of (a) has a pH of about 4.0 to about 5.0, and the composition after (d) has a pH of about 4.0 to about 5.0. In some embodiments, the composition of (a) has a pH of 4.3 to 4.7, and the composition after (d) has a pH of 4.3 to 4.7.

In some embodiments, the composition of (d) comprises less than 0.3% (wt/wt) of Impurity A, Impurity B, Impurity C, Impurity D, Impurity E or Impurity F. In some embodiments, the composition of (d) comprises less than 0.2% (wt/wt) of Impurity A, Impurity B, Impurity C, Impurity D, Impurity E or Impurity F. In some embodiments, the composition of (d) comprises less than 1.0% (wt/wt) of Impurity A, Impurity B, Impurity C, Impurity D, Impurity E and Impurity F. In some embodiments, the composition of (d) comprises less than 0.5% (wt/wt) of Impurity A, Impurity B, Impurity C, Impurity D, Impurity E and Impurity F.

In some embodiments, the method comprises a composition comprising sodium chloride, wherein the sodium chloride is about 5 mg/mL to about 12 mg/mL in the composition.

In some embodiments, the method comprises a composition comprising sodium chloride, wherein the sodium chloride is about 5.5 mg/mL to about 9 mg/mL in the composition.

In some embodiments, the method comprises a composition comprising sodium chloride, wherein the sodium chloride is about 7.5 mg/mL in the composition.

In some embodiments, the method comprises a composition, wherein the composition does not comprise a preservative.

In some embodiments, the method comprises a composition comprising sodium chloride, wherein the composition does not comprise an antimicrobial agent.

In some embodiments, the disclosure provides a method of sterilizing a lacosamide composition, the method comprising; (a) obtaining a composition comprising (i) lacosamide, (ii) sodium chloride, and (iii) water, (b) placing the composition of (a) into a glass vial, wherein the glass vial has an ammonium sulfate coating, (c) sealing the composition inside the glass vial; and (d) sterilizing the sealed glass vial of (c).

In some embodiments, the disclosure provides a method of making a lacosamide intravenous solution, the method comprising; (a) obtaining a composition comprising (i) lacosamide, (ii) sodium chloride, and (iii) water, (b) placing the composition of (a) into a glass vial, wherein the glass vial has an ammonium sulfate coating, (c) sealing the composition inside the glass vial; (d) sterilizing the sealed glass vial of (c) comprising the composition; and (e) diluting the sterilized composition of (d) with conventional diluents used for intravenous administration, for administration to a patient in need of lacosamide therapy.

In some embodiments, the disclosure is directed to a sterile lacosamide composition made by any one of the methods described herein.

The present disclosure is directed to a package comprising: (a) a composition having pH of about 3.5 to about 5.0 comprising: (i) lacosamide, (ii) sodium chloride, and (iii) water, wherein the composition comprises less than 1% (wt/wt) of total impurities; and (b) a glass vial with an ammonium sulfate coating, wherein the composition is sterile.

In some embodiments, the composition has a pH of about 4.0 to about 5.0. In some embodiments, the composition has a pH of about 4.3 to about 4.7.

In some embodiments, the composition comprises less than 0.3% (wt/wt) of Impurity A, Impurity B, Impurity C, Impurity D, Impurity E or Impurity F. In some embodiments, the composition comprises less than 0.2% (wt/wt) of Impurity A, Impurity B, Impurity C, Impurity D, Impurity E or Impurity F. In some embodiments, the composition comprises less than 1.0% (wt/wt) of Impurity A, Impurity B, Impurity C, Impurity D, Impurity E and Impurity F. In some embodiments, the composition comprises less than 0.5% (wt/wt) of Impurity A, Impurity B, Impurity C, Impurity D, Impurity E and Impurity F.

In some embodiments, the sodium chloride is about 5 mg/mL to about 12 mg/mL in the composition. In some embodiments, the sodium chloride is about 5.5 mg/mL to about 9 mg/mL in the composition. In some embodiments, the sodium chloride is about 7.5 mg/mL in the composition.

In some embodiments, the composition does not comprise a preservative. In some embodiments, the composition does not comprise an antimicrobial agent.

DETAILED DESCRIPTION

Sterilization of a drug product, and prevention of contamination is critical in the manufacturing of therapeutic infusions. Typically, two methods of sterilization are utilized: (i) aseptic processing, and (ii) terminal sterilization. In aseptic processing, the manufacturing process is conducted in contained areas with defined microbial loads, and the resulting product is monitored at each stage of the production process for bioburden, often with a sterilization step, e.g., filtration, before packaging. However, terminal sterilization is often preferred to aseptic processing. Terminal sterilization is a method by which the product is sterilized in the final container or at the time of packaging. Terminal sterilization provides a more consistent and reliable manner of microbial destruction. For terminal sterilization, the product is filled in a final container and is subjected to high temperature under pressure, e.g., in an autoclave. Typical terminal sterilization involves, autoclaving at 121° C. and 15 lbs pressure for 15 minutes. However, the present disclosure reports that terminal sterilization of lacosamide injection solution leads to change in pH of the solution, leading to degradation of lacosamide. The present disclosure provides a method of terminally sterilizing a lacosamide solution without impacting its stability, i.e., wherein the lacosamide solution does not change pH and does not form increased impurities upon terminal sterilization.

In some embodiments, the present disclosure is directed to a package comprising a lacosamide composition, e.g., a lacosamide drug product, e.g., a lacosamide injection, a lacosamide infusion, or other aqueous-based lacosamide formulation. The term "package" as used herein can include any package suitable for the storage and/or administration of the lacosamide formulation. Suitable packages can include a glass vial (or other enclosed glass containers suitable for storing the lacosamide formulation such as flexible plastic containers and prefilled syringes). In some embodiments, the package comprises: (a) a composition comprising (i) lacosamide, (ii) sodium chloride, and (iii) water, wherein the composition has a pH of about 3.5 to about 5.0; and (b) a glass vial, wherein the glass vial has an ammonium sulfate coating, and wherein the composition is sterile. In some embodiments, the package further comprises a stopper, e.g., a rubber stopper or other means for enclosing or stoppering the vial. In some embodiments, the package further comprises a means for securing the stopper on the glass vial. In some embodiments, the package further comprises a label, e.g., a label identifying the product, the amount/strength of the product, and/or other information pertinent to the product, e.g., methods of administration, dosages and regimens, adverse effects associated with the formulation, contraindications, etc.

In some embodiments, the glass vial has an ammonium sulfate coating. In some embodiments, vial coating can be added prior to the annealing step during a vial manufacturing process to react with the sodium on the glass surface. In some embodiments, the ammonium sulfate coating produces sodium sulfate, which is highly water soluble and can be removed in a subsequent washing step and is used to dealkalize the glass surface. While glass vials are predominantly used for packaging of liquid formulations such as injections, when glass vials comprising a liquid drug product are autoclaved, formation of visible and sub-visible flakes has been reported. The formation of particulates in liquid drug products can be a serious problem and has resulted in recalls of the drug product. Further, the active pharmaceutical ingredient(s) and excipients may interact with glass in the vial, resulting in delamination of the inner surface of the glass vial, thereby producing additional particles. Interaction of particulates with the drug product can reduce the efficacy of the drug and may lead to side effects due to leaching of glass elements into the formulation. Leaching of metal ion from the glass vial could also lead to altering the pH, stability of the drug, and reduction in efficacy.

Vials coated with ammonium sulfate can be made by methods known in the art, and are commercially available, e.g., from Borosil® Klasspack (Mumbai, India) or SGD Pharma (Puteaux, France). The phrase "glass vial has an ammonium sulfate coating . . . ." does not preclude the existence of other coatings on the vial, or any other embodiments or elements on the vial. The ammonium sulfate coating has been reported to result in a greater degree of surface pitting relative to non-coated vials. Additionally, vials coated with ammonium sulfate were expected to be prone to delamination more than untreated vials, which might be caused by significant extraction of the alkali oxides. Thus, due to these reported limitations of the coating, prior to the present disclosure, the skilled artisan would not necessarily have been directed to use coated vials, e.g., vials coated with ammonium sulfate, and would have been dissuaded from using the same for terminally sterilizing a lacosamide composition in such vials. Further, applicants also observed that the pH of the lacosamide composition would shift by more than 1 pH unit after autoclaving the composition. This shift in pH led to degradation of lacosamide in the composition. However, the applicants have now found a process by which a composition of lacosamide containing 5 mg/ml to 9 mg/ml of sodium chloride and water can be terminally sterilized in coated glass vials, while maintaining the pH of the composition and ensuring that the impurities remain within predefined limits. Contrary to reported issues with coated vials (discussed above), applicants were able to obtain a sterile and stable composition of lacosamide, as described herein.

In some embodiments, the lacosamide is about 0.005% to about 5% (wt/vol), about 0.01% to about 3% (wt/vol), about 0.03% to about 1% (wt/vol), about 0.05% to about 0.5% (wt/vol), about 0.07% to about 0.3% (wt/vol), or about 0.08% to about 0.15% (wt/vol) of the composition. In some embodiments, the lacosamide is 0.08%, 0.09%, 0.1%, 0.12%, 0.14%, 0.16%, 0.18%, 0.2%, 0.3%, 0.4%, 0.5%, 0.6%, 0.7%, 0.8% or 1% (wt/vol) of the composition. In some embodiments, the lacosamide is about 1 mg/mL to about 100 mg/mL, about 2 mg/mL to about 50 mg/mL, about 5 mg/mL to about 20 mg/mL, about 8 mg/mL to about 12 mg/mL or about 10 mg/mL.

The composition comprising lacosamide can have a pH in the range of about 4.0 to about 5.0. In some embodiments, the composition has a pH from about 4.3 to about 4.7. The present disclosure provides for compositions that have a pH that does not change after the composition is terminally sterilized. Thus, the present disclosure provides for sterile lacosamide compositions which have been terminally sterilized, e.g., via autoclave, wherein the pH of the composition does not substantially change during and after the terminal sterilization. In some embodiments, the pH of the composition before and after terminal sterilization has a difference of less than 1.0 unit. In some embodiments, the pH of the composition has a difference of less than 0.6 units, when measured before and after terminal sterilization.

In some embodiments, the package comprises: (a) a composition comprising (i) about 5 mg/mL to about 15 mg/mL lacosamide, (ii) about 5.5 mg/mL to about 9 mg/mL sodium chloride, and (iii) water, wherein the composition has a pH of about 4.3 to about 4.7; and wherein the composition is sterile; and (b) a glass vial, wherein the glass vial has an ammonium sulfate coating.

In some embodiments, the package comprises: (a) a composition comprising (i) about 10 mg/mL lacosamide, (ii) 7.5 mg/mL sodium chloride, and (iii) water, wherein the composition has a pH of about 4.3 to about 4.7; and (b) a glass vial with an ammonium sulfate coating, and wherein the composition is sterile.

The present disclosure also provides for sterile liquid lacosamide formulations, which have been terminally sterilized, and which have reduced amounts of impurities. Some of the known impurities, e.g., degradation impurities from lacosamide, are found in Table 6 herewith, and can be determined by means known in the art, e.g., liquid chromatography, e.g., HPLC, mass spectroscopy, etc.

In some embodiments, the composition comprises less than 0.3% (wt/wt) of Impurity A, Impurity B, Impurity C, Impurity D, Impurity E or Impurity F. In some embodiments, the composition comprises less than 0.3% (wt/wt) each of Impurity A, and Impurity B. In some embodiments, the composition comprises less than 0.3% (wt/wt) each of Impurity A, Impurity B, and Impurity C. In some embodiments, the composition comprises less than 0.3% (wt/wt) each of Impurity A, Impurity B, Impurity C, and Impurity D. In some embodiments, the composition comprises less than 0.3% (wt/wt) each of Impurity A, Impurity B, Impurity C, Impurity D, and Impurity E. In some embodiments, the composition comprises less than 0.3% (wt/wt) each of Impurity A, Impurity B, Impurity C, Impurity D, Impurity E and Impurity F. In some embodiments, the composition comprises less than 0.3% (wt/wt) each of Impurity B and Impurity C. In some embodiments, the composition comprises less than 0.3% (wt/wt) each of Impurity B, Impurity C, and Impurity D. In some embodiments, the composition comprises less than 0.3% (wt/wt) each of Impurity B, Impurity C, Impurity D, and Impurity E. In some embodiments, the composition comprises less than 0.3% (wt/wt) each of Impurity B, Impurity C, Impurity D, Impurity E and Impurity F. In some embodiments, the composition comprises less than 0.3% (wt/wt) each of Impurity C and Impurity D. In some embodiments, the composition comprises less than 0.3% (wt/wt) each of Impurity C, Impurity D, and Impurity E. In some embodiments, the composition comprises less than 0.3% (wt/wt) each of Impurity C, Impurity D, Impurity E and Impurity F. In some embodiments, the composition comprises less than 0.3% (wt/wt) each of Impurity D and Impurity E. In some embodiments, the composition comprises less than 0.3% (wt/wt) each of Impurity D, Impurity E and Impurity F.

In some embodiments, the composition comprises less than 0.2% (wt/wt) of Impurity A, Impurity B, Impurity C, Impurity D, Impurity E or Impurity F. In some embodiments, the composition comprises less than 0.2% (wt/wt) each of Impurity A, and Impurity B. In some embodiments, the composition comprises less than 0.2% (wt/wt) each of Impurity A, Impurity B, and Impurity C. In some embodiments, the composition comprises less than 0.2% (wt/wt) each of Impurity A, Impurity B, Impurity C, and Impurity D. In some embodiments, the composition comprises less than 0.2% (wt/wt) each of Impurity A, Impurity B, Impurity C, Impurity D, and Impurity E. In some embodiments, the composition comprises less than 0.2% (wt/wt) each of Impurity A, Impurity B, Impurity C, Impurity D, Impurity E and Impurity F. In some embodiments, the composition comprises less than 0.2% (wt/wt) each of Impurity B and Impurity C. In some embodiments, the composition comprises less than 0.2% (wt/wt) each of Impurity B, Impurity C, and Impurity D. In some embodiments, the composition comprises less than 0.2% (wt/wt) each of Impurity B, Impurity C, Impurity D, and Impurity E. In some embodiments, the composition comprises less than 0.2% (wt/wt) each of Impurity B, Impurity C, Impurity D, Impurity E and Impurity F. In some embodiments, the composition comprises less than 0.2% (wt/wt) each of Impurity C and Impurity D. In some embodiments, the composition comprises less than 0.2% (wt/wt) each of Impurity C, Impurity D, and Impurity E. In some embodiments, the composition comprises less than 0.2% (wt/wt) each of Impurity C, Impurity D, Impurity E and Impurity F. In some embodiments, the composition comprises less than 0.2% (wt/wt) each of Impurity D and Impurity E. In some embodiments, the composition comprises less than 0.2% (wt/wt) each of Impurity D, Impurity E and Impurity F.

In some embodiments, the composition comprises less than 0.1% (wt/wt) of Impurity A, Impurity B, Impurity C, Impurity D, Impurity E or Impurity F. In some embodiments, the composition comprises less than 0.1% (wt/wt) each of Impurity A, and Impurity B. In some embodiments, the composition comprises less than 0.1% (wt/wt) each of Impurity A, Impurity B, and Impurity C. In some embodiments, the composition comprises less than 0.1% (wt/wt) each of Impurity A, Impurity B, Impurity C, and Impurity D. In some embodiments, the composition comprises less than 0.1% (wt/wt) each of Impurity A, Impurity B, Impurity C, Impurity D, and Impurity E. In some embodiments, the composition comprises less than 0.1% (wt/wt) each of Impurity A, Impurity B, Impurity C, Impurity D, Impurity E and Impurity F. In some embodiments, the composition comprises less than 0.1% (wt/wt) each of Impurity B and Impurity C. In some embodiments, the composition comprises less than 0.1% (wt/wt) each of Impurity B, Impurity C, and Impurity D. In some embodiments, the composition comprises less than 0.1% (wt/wt) each of Impurity B, Impurity C, Impurity D, and Impurity E. In some embodiments, the composition comprises less than 0.1% (wt/wt) each of Impurity B, Impurity C, Impurity D, Impurity E and Impurity F. In some embodiments, the composition comprises less than 0.1% (wt/wt) each of Impurity C and Impurity D. In some embodiments, the composition comprises less than 0.1% (wt/wt) each of Impurity C, Impurity D, and Impurity E. In some embodiments, the composition comprises less than 0.1% (wt/wt) each of Impurity C, Impurity D, Impurity E and Impurity F. In some embodiments, the composition comprises less than 0.1% (wt/wt) each of Impurity D and Impurity E. In some embodiments, the composition comprises less than 0.1% (wt/wt) each of Impurity D, Impurity E and Impurity F.

In some embodiments, the composition comprises less than 1.0% (wt/wt) of Impurity A, Impurity B, Impurity C, Impurity D, Impurity E and Impurity F. In some embodiments, the composition comprises less than 0.5% (wt/wt) of Impurity A, Impurity B, Impurity C, Impurity D, Impurity E and Impurity F.

The compositions of the present disclosure can comprise various concentration of tonicity modifiers such as sodium chloride. In some embodiments, the sodium chloride is about 5 mg/mL to about 12 mg/mL in the composition. In some embodiments, the sodium chloride is about 5.5 mg/mL to about 9 mg/mL in the composition. In some embodiments, the sodium chloride is present in an amount of about 7.5 mg/mL in the composition.

In some embodiments, the disclosure provides a sterile composition comprising a solution of lacosamide and pharmaceutically acceptable excipients, having a pH of about 3.5 to about 5.0, wherein the composition is terminally sterilized by autoclaving the said solution in a glass vial coated with ammonium sulfate, such that the pH of the said composition after terminal sterilization remains within +/−1.0 unit of the pH of the composition prior to terminal sterilization, wherein the composition has an impurity profile such that each of Impurity A, Impurity B, Impurity C, Impurity D, Impurity E and Impurity F is less than 0.5% (wt/wt).

In some embodiments, the compositions described herein, which are achieved by terminal sterilization, do not require an antimicrobial agent and/or a preservative. In some embodiments, the composition does not comprise a preservative. In some embodiments, the composition does not comprise an antimicrobial agent.

The disclosure provided herein is directed to methods for making a sterile lacosamide formulation, e.g., an aqueous formulation, e.g., a lacosamide injection or a lacosamide infusion. In some embodiments, the disclosure is directed to a method of making a sterile lacosamide formulation, the method comprising; (a) obtaining a composition comprising (i) lacosamide, (ii) sodium chloride, and (iii) water, (b) placing the composition of (a) into a glass vial, wherein the glass vial has an ammonium sulfate coating, (c) sealing the composition inside the glass vial; and (d) sterilizing the sealed glass vial of (c).

In some embodiments, the disclosure provides a method of sterilizing a lacosamide composition, the method comprising; (a) obtaining a composition comprising (i) lacosamide, (ii) sodium chloride, and (iii) water, (b) placing the composition of (a) into a glass vial, wherein the glass vial has an ammonium sulfate coating, (c) sealing the composition inside the glass vial; and (d) sterilizing the sealed glass vial of (c).

In some embodiments, the disclosure provides a method of making a lacosamide intravenous solution, the method comprising; (a) obtaining a composition comprising (i) lacosamide, (ii) sodium chloride, and (iii) water, (b) placing the composition of (a) into a glass vial, wherein the glass vial has an ammonium sulfate coating, (c) sealing the composition inside the glass vial; (d) sterilizing the sealed glass vial of (c) comprising the composition; and (e) diluting the sterilized composition of (d) with a conventional diluent solution to provide an intravenous solution for administration.

In some embodiments, the method provides for sealing the composition inside the glass vial. Methods of sealing a composition inside a glass bottle include, e.g., placing a stopper, e.g., a rubber stopper or other object over the mouth of the vial, thereby preventing contamination of the composition inside the vial, followed by final sealing and crimping of the vial after the terminal sterilization. Thus, in some embodiments, the disclosure provides a method of making a sterile lacosamide formulation by terminally sterilizing the composition inside a coated glass vial.

Methods for sterilizing are known in the art, and include, e.g., autoclaving. In some embodiments, the sealed glass vial is autoclaved at 110° C. to 150° C., 115° C. to 140° C., or 120° C. to 130° C. at 10-30 lbs pressure, 12-25 lbs pressure, or 14-18 lbs pressure. The skilled artisan will also appreciate that the amount of pressure needed during the elevated temperatures will be related to the temperature of the autoclave. In some embodiments, the autoclave sterilization is performed at 121° C./15 lbs pressure. The duration of the autoclave sterilization can also be adjusted. In some embodiments, the autoclave sterilization is for 10 minutes to 1 hour, 10 minutes to 30 minutes or 10 minutes to 20 minutes. In the present disclosure, the autoclave sterilization is performed at 121° C./15 lbs pressure for 15 minutes.

In some embodiments, when performing the methods described herein, the pH of the composition in step (d) of the method is substantially the same as the pH of the composition in step (a) of the method. In some embodiments, the pH of the composition of (a) and the pH of the composition after (d) have a difference of less than 1.0 unit. In some embodiments, the pH of the composition of (a) and the pH of the composition after (d) have a difference of less than 0.6 units. In some embodiments, the composition of (a) has a pH of about 4.0 to about 5.0, and the composition after (d) has a pH of about 4.0 to about 5.0. In some embodiments, the composition of (a) has a pH of about 4.3 to about 4.7, and the composition after (d) has a pH of about 4.3 to about 4.7.

In some embodiments, the composition of (d) comprises less than 0.3% (wt/wt) of Impurity A, Impurity B, Impurity C, Impurity D, Impurity E or Impurity F. In some embodiments, the composition of (d) comprises less than 0.2% (wt/wt) of Impurity A, Impurity B, Impurity C, Impurity D, Impurity E or Impurity F. In some embodiments, the composition of (d) comprises less than 1.0% (wt/wt) of Impurity A, Impurity B, Impurity C, Impurity D, Impurity E and Impurity F. In some embodiments, the composition of (d) comprises less than 0.5 (wt/wt) of Impurity A, Impurity B, Impurity C, Impurity D, Impurity E and Impurity F.

In some embodiments, the disclosure is directed to a sterile lacosamide composition made by any one of the methods described herein.

Thus, the present disclosure provides a method for producing a liquid lacosamide composition using terminal sterilization, wherein the composition does not change pH and/or increase in impurities after the terminal sterilization.

EXAMPLES

Example 1: The Effect of Terminal Sterilization on Lacosamide Drug Product

Lacosamide formulations qualitatively similar to Vimpat were produced with consistent amounts of lacosamide and varying amounts of sodium chloride, and filled in untreated glass vials. Terminal sterilization was carried out by autoclaving at a pressure of 121° C./15 lbs pressure for 15 minutes. Product was then tested after terminal sterilization. The results are included in Table 1 below.

TABLE 1

Results of pH after Terminal Sterilization in USP Type-I Clear Glass vials (Untreated)

| Details of Composition | pH before Terminal sterilization | pH after Terminal sterilization |
|---|---|---|
| Sodium chloride: 5.5 mg/mL | 4.36 | 6.73 |
| Sodium Chloride: 7.5 mg/mL | 4.34 | 5.90 |
| Sodium Chloride: 9.0 mg/mL | 4.44 | 6.52 |

Table 1 demonstrates that terminal sterilization affected the pH of each of the lacosamide formulations.

Example 2: Results of pH after Terminal Sterilization in USP Type-I Clear Glass Vials (Ammonium Sulfate Treated Vials Manufactured by Borosil Klasspack)

Further tests were conducted to discover whether treatment of the glass vials by coating, e.g., spraying, ammonium sulfate on the glass before the annealing step, and before filling with lacosamide drug product would increase the pH stability of the drug product after terminal stabilization. While not being bound to any theory, in some embodiments ammonium sulfate glass vial treatments reduce the alkalinity of the glass surface after terminal sterilization. In some embodiments, ammonium sulfate treatment can substantially reduce the delamination that occurs during autoclaving when compared with untreated vials.

The finished lacosamide drug product was filled into ammonium sulfate treated vials (manufactured by Borosil Klasspack) and terminally sterilized at 121° C./15 lbs pressure for 15 minutes. See Table 2.

TABLE 2

Results of pH after Terminal Sterilization in ammonium sulfate treated vials (Borosil ® Klasspack)

| Details of Composition | pH before Terminal sterilization | pH after Terminal sterilization |
|---|---|---|
| Sodium chloride: 5.5 mg/mL | 4.36 | 4.55 |
| Sodium Chloride: 7.5 mg/mL | 4.34 | 4.47 |
| Sodium Chloride: 9.0 mg/mL | 4.44 | 4.63 |

No significant change in pH was observed for the drug product at different concentrations of sodium chloride when terminally sterilized in glass vials treated with ammonium sulfate.

Example 3: Results of pH after Terminal Sterilization in Ammonium Sulfate Treated Vials (Sgd Pharma)

The experiment of Example 2 was repeated but the composition was filled in ammonium sulfate treated vials from a different supplier, SGD Pharma instead of from Borosil Klasspack. The finished product was terminally sterilized at 121° C./15 lbs pressure for 15 minutes. See Table 3.

TABLE 3

Results of pH after Terminal Sterilization in ammonium sulfate treated vials (SGD Pharma)

| Details of Composition | pH before Terminal sterilization | pH after Terminal sterilization |
|---|---|---|
| Sodium chloride: 5.5 mg/mL | 4.36 | 4.62 |
| Sodium Chloride: 7.5 mg/mL | 4.34 | 4.38 |
| Sodium Chloride: 9.0 mg/mL | 4.44 | 4.64 |

The change in pH post terminal sterilization was found to be within acceptable limits.

Examples 2 and 3 provide evidence that use of vials treated with ammonium sulfate, when used for packing lacosamide solution, avoid changes to the pH in the drug formulations, i.e., reduces pH drift, post terminal sterilization. Such treated glass vials were, therefore, considered for filling and terminal sterilization of the lacosamide solution. Upon terminal sterilization in treated, clear USP Type-I glass vials, the pH was found to stay stable.

Example 4—the Effect of Terminal Sterilization on Lacosamide Stability

The effect on lacosamide stability was investigated in the formulations terminally sterilized in glass vials treated with ammonium sulfate. The lacosamide composition was packaged in treated glass vials and autoclaved. The composition had an impurity profile as defined in Table 2 below after terminal sterilization:

TABLE 4

Impurity profile of the stable parenteral composition of lacosamide of the present invention

| Impurity | Specification |
| --- | --- |
| Impurity-A | Not more than 0.2% |
| Impurity-B | Note more than 0.2% |
| Impurity-C | Not more than 0.2% |
| Impurity-D | Not more than 0.2% |
| Impurity-E | Not more than 0.2% |
| Impurity-F | Not more than 0.2% |
| Any unspecified impurity | Not more than 0.2% |
| Total impurities | Note more than 1% |

The impurities mentioned in Table 4 above have the structures and nomenclature, as shown in Table 5 below.

TABLE 5

Impurity details

| Impurity | Structure | Nomenclature |
| --- | --- | --- |
| A | 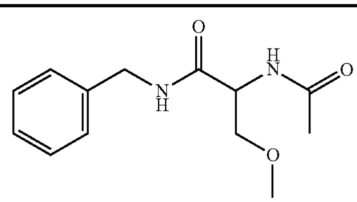 | (R)-N-Benzyl-2-acetamido-3-methoxypropionamide |
| B | 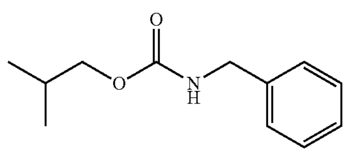 | Benzyl-carbamic acid isobutyl ester |
| C | 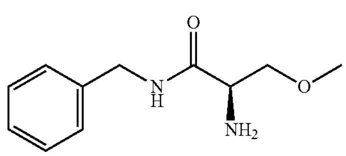 | (R)-2-Amino-N-benzyl-3-methoxypropionamide |
| D | 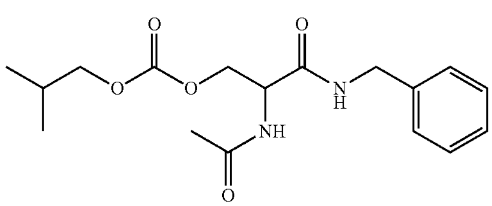 [SMILES: CC(=O)NC(COC(=O)OCC(C)C)C(=O)NCc1ccccc1] | Carbonic acid (R)-2-acetylamino-2-benzylcarbamoyl-ethyl ester isobutyl ester |
| E | 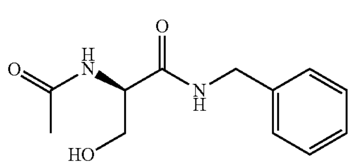 [SMILES: CC(=O)N[C@H](CO)C(=O)NCc1ccccc1] | (R)-2-Acetylamino-N-benzyl-3-hydroxy-propionamide |
| F | 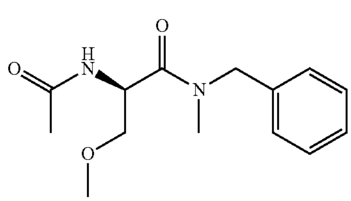 [SMILES: COC[C@@H](NC(C)=O)C(=O)N(C)Cc1ccccc1] | (R)-2-Acetylamino-N-benzyl-3-methoxy-N-methyl-propionamide |

Thus, terminal sterilization did not increase the impurities in the lacosamide formulations.

Example 5: Chemical Characterization of Lacosamide Injection after Terminal Sterilization in Coated and Uncoated Vials Different batches of lacosamide product were autoclaved at uniform concentration of sodium chloride (7.5 mg/ml). Batches 1 and 2 were autoclaved in vials treated with ammonium sulfate. Batch 3 was autoclaved in untreated vials. The impurity percentages were calculated as found in Table 6.

TABLE 6

Impurity profile of the stable parenteral composition of lacosamide in untreated vials, and vials treated with ammonium sulfate.

| Batch # | 1 | 2 | 3 |
|---|---|---|---|
| | | Impurities | |
| Maximum unspecified impurity | 0.13 | 0.11 | 0.38 |
| Total impurity | 0.38 | 0.35 | 0.55 |
| Details of vials in which product is autoclaved | Ammonium sulfate treated 20 ml USP Type-I Glass vials | | Untreated 20 ml USP Type-I Glass vials |

Table 6 demonstrates that ammonium sulfate treated vials show a lower total impurity percentage when compared to untreated vials.

What is claimed is:

1. A method of making a sterile lacosamide composition, the method comprising;
   a. obtaining a composition comprising (i) about 5 mg/mL to about 20 mg/mL lacosamide, (ii) about 5.5 mg/mL to about 9 mg/mL sodium chloride, and (iii) water,
   b. placing the composition of (a) into a glass vial, wherein the glass vial has an ammonium sulfate coating,
   c. sealing the composition inside the glass vial; and
   d. autoclaving the sealed glass vial of (c) at 121° C. at 15 psi for 1.5 minutes,
   wherein the pH of the composition in (d) is substantially the same as the pH of the composition after (a), and wherein the composition of (d) comprises less than about 0.2% (wt/wt) of Impurity A, Impurity B, Impurity C, Impurity D, Impurity E or Impurity F.

2. The method of claim 1, wherein the pH of the composition of (a) and the pH of the composition after (d) have a difference of less than 1.0 unit.

3. The method of claim 1, wherein the pH of the composition of (a) and the pH of the composition after (d) have a difference of less than 0.6 unit.

4. The method of claim 1, wherein the composition of (a) has a pH of about 4.0 to about 5.0, and the composition after (d) has a pH of about 4.0 to about 5.0.

5. The method of claim 1, wherein the composition of (a) has a pH of about 4.3 to about 4.7, and the composition after (d) has a pH of about 4.3 to about 4.7.

6. The method of claim 1, wherein the composition of (d) comprises less than about 0.2% (wt/wt) each of Impurity A, Impurity B, Impurity C, Impurity D, Impurity E or Impurity F.

7. The method of claim 1, wherein the composition of (d) comprises less than about 1.0% (wt/wt) of Impurity A, Impurity B, Impurity C, Impurity D, Impurity E and Impurity F.

8. The method of claim 1, wherein the sodium chloride is about 7.5 mg/mL in the composition.

9. The method of claim 1, wherein the composition does not comprise a preservative.

10. The method of claim 1, wherein the composition does not comprise an antimicrobial agent.

* * * * *

UNITED STATES PATENT AND TRADEMARK OFFICE
CERTIFICATE OF CORRECTION

PATENT NO. : 11,278,634 B1
APPLICATION NO. : 17/327308
DATED : March 22, 2022
INVENTOR(S) : Krishna Mohan Chilakala, Hanumantha Rao Kamma and Janos Vaczi It is certified that error appears in the above-identified patent and that said Letters Patent is hereby corrected as shown below:

In the Claims

Claim 1, Column 13, Lines 27-28 replace "d. autoclaving the sealed glass vial of (c) at 121 °C at 15 psi for 1.5 minutes," with --d. autoclaving the sealed glass vial of (c) at 121° C. at 15 psi for 15 minutes,--

Signed and Sealed this
Fourteenth Day of May, 2024

Katherine Kelly Vidal
*Director of the United States Patent and Trademark Office*